(12) United States Patent
Weiss et al.

(10) Patent No.: US 9,975,820 B2
(45) Date of Patent: May 22, 2018

(54) PROCESS FOR XYLENES ISOMERIZATION

(71) Applicant: ExxonMobil Chemical Patents Inc., Baytown, TX (US)

(72) Inventors: Brian M. Weiss, Bridgewater, NJ (US); Darryl D. Lacy, Easton, PA (US); Scott J. Weigel, Allentown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/722,961

(22) Filed: Oct. 2, 2017

(65) Prior Publication Data
US 2018/0022669 A1 Jan. 25, 2018

Related U.S. Application Data

(62) Division of application No. 15/296,878, filed on Oct. 18, 2016, now Pat. No. 9,809,509.

(60) Provisional application No. 62/267,428, filed on Dec. 15, 2015.

(51) Int. Cl.
*C07C 5/27* (2006.01)
*C07C 4/18* (2006.01)

(52) U.S. Cl.
CPC ............. *C07C 5/2737* (2013.01); *C07C 4/18* (2013.01); *C07C 2529/40* (2013.01); *C07C 2529/70* (2013.01)

(58) Field of Classification Search
CPC ....................................................... C07C 5/27

USPC ................................................. 585/481, 478
See application file for complete search history.

(56) References Cited

U.S. PATENT DOCUMENTS

| 3,354,078 | A | | 11/1967 | Miale et al. |
| 3,770,841 | A | * | 11/1973 | Meyers, Jr. ........... C07C 5/2708 585/478 |
| 4,016,218 | A | | 4/1977 | Haag et al. |
| 4,104,151 | A | * | 8/1978 | Rubin ..................... B01J 29/70 208/111.15 |
| 4,694,114 | A | * | 9/1987 | Chu ........................ B01J 29/44 585/481 |
| 5,516,956 | A | | 5/1996 | Abichandani et al. |
| 7,271,118 | B2 | | 9/2007 | Raich et al. |
| 7,663,010 | B2 | | 2/2010 | Levin |

OTHER PUBLICATIONS

Miale et al., "Catalysis by Crystalline Aluminosilicates IV. Attainable Catalytic Cracking Rate Constants, and Superactivity", Journal of Catalysis, vol. 6, Issue 2, pp. 278-287 (1966).

(Continued)

*Primary Examiner* — Thuan D Dang

(57) ABSTRACT

A process for the isomerization of a para-xylene depleted, meta-xylene rich stream under at least partially liquid phase conditions using ZSM-23 with an external surface area of at least 75 m²/g (indicating a small crystallite size), and a SiO$_2$/Al$_2$O$_3$ ratio between 15 and 75 that produces a higher than equilibrium amount of para-xylene, i.e., more than about 24 wt % of para-xylene, based on the total amount of xylenes.

8 Claims, 2 Drawing Sheets

(56) References Cited

OTHER PUBLICATIONS

Olson et al., "Chemical and Physical Properties of the ZSM-5 Substitutional Series", Journal of Catalysis, vol. 61, Issue 2, pp. 390-396 (1980).
Weisz et al., "Superactive Crystalline Aluminosilicate Hydrocarbon Catalysts", Journal of Catalysis, vol. 4, Issue 4, pp. 527-529 (1965).

* cited by examiner

PROCESS FOR XYLENES ISOMERIZATION

PRIORITY

This application is a divisional of U.S. patent application Ser. No. 15/296,878, filed Oct. 18, 2016, which claims priority to and the benefit of U.S. Provisional Patent Application Ser. No. 62/267,428, filed Dec. 15, 2015, the contents of each being incorporated herein by reference herein in their entireties for all purposes.

FIELD OF THE INVENTION

This invention relates to an improved xylenes isomerization process.

BACKGROUND OF THE INVENTION

Para-xylene (PX) is a valuable chemical feedstock, which may be derived from mixtures of $C_8$ aromatics separated from such raw materials as petroleum naphthas, particularly reformates. The $C_8$ aromatic fractions from these sources vary quite widely in composition but, in the case of a reformate stream, will usually comprise 10 to 32 wt % ethylbenzene (EB) with the balance, xylenes, being divided between approximately 50 wt % of meta-xylene (MX) and 25 wt % each of para-xylene and ortho-xylene (OX). Of these isomers, para-xylene is by far the most important for commercial applications.

Individual isomer products may be separated from the naturally occurring $C_8$ aromatic mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption or simulated moving bed chromatography (e.g., the Parex™ or Eluxyl® process), or membrane separation.

As commercial use of para-xylene has increased, combining physical separation with chemical isomerization of the other xylene isomers to increase the yield of the desired para-isomer has become increasingly important. Prior art commercial processes separate para-xylene from the other xylene isomers and isomerize the para-depleted stream over ZSM-5, producing an equilibrium mixture of xylenes, which contains about 23 wt % or less of para-xylene, based on the total amount of xylenes in the isomerized stream. The isomerized stream is then recycled to the para-xylene separation step, forming what is commonly known as the xylenes loop. Because of the relatively low amount of para-xylene produced in the xylenes loop, there is a substantial degree of recycling, requiring a substantial amount of energy. Thus, there is an ongoing need for improved xylene isomerization catalysts and processes.

SUMMARY OF THE INVENTION

The present invention is directed to a process for the isomerization of a para-xylene depleted, meta-xylene rich stream under at least partially liquid phase conditions using ZSM-23 with an external surface area of at least 75 m²/g (indicating a small crystallite size), and a $SiO_2/Al_2O_3$ ratio between 15 and 75 that produces a higher than equilibrium amount of para-xylene, i.e., more than about 24 wt % of para-xylene, based on the total amount of xylenes. The catalyst used in the inventive process converts meta-xylene to para-xylene while forming only a small amount of ortho-xylene.

In one embodiment, a $C_8$ aromatic hydrocarbon mixture comprising para-xylene, ortho-xylene and meta-xylene is provided to an ortho-xylene splitter to produce a first stream comprising para-xylene and meta-xylene and a second stream comprising ortho-xylene. The first stream comprising para-xylene and meta-xylene passes to a para-xylene recovery unit to recover a para-xylene product stream and produce a para-xylene-depleted stream comprising meta-xylene, which is contacted with a catalyst under at least partially liquid phase conditions effective to produce a first isomerized stream having a para-xylene content of more than about 24 wt %, based on the total amount of xylenes in the first isomerized stream. At least a portion of the first isomerized stream is then recycled back to the para-xylene recovery unit. Optionally, the second stream comprising ortho-xylene is contacted with a catalyst comprising ZSM-5 having an alpha value of at least 300 under at least partially liquid phase conditions effective to produce a second isomerized stream, at least a portion of which is recycled back to the ortho-xylene splitter.

DETAILED DESCRIPTION

The present invention is directed to a process for the isomerization of a para-xylene depleted, meta-xylene rich stream using ZSM-23 with an external surface area of at least 75 m²/g (indicating a small crystallite size), and higher aluminum content that produces a higher than equilibrium amount of para-xylene, i.e., more than about 24 wt % of para-xylene, based on the total amount of xylenes. The smaller crystal size and higher aluminum content allows the isomerization reaction to be conducted at lower temperatures than isomerization processes using larger crystal ZSM-23 catalysts, which in turn produces a better product yield.

Figure 1:
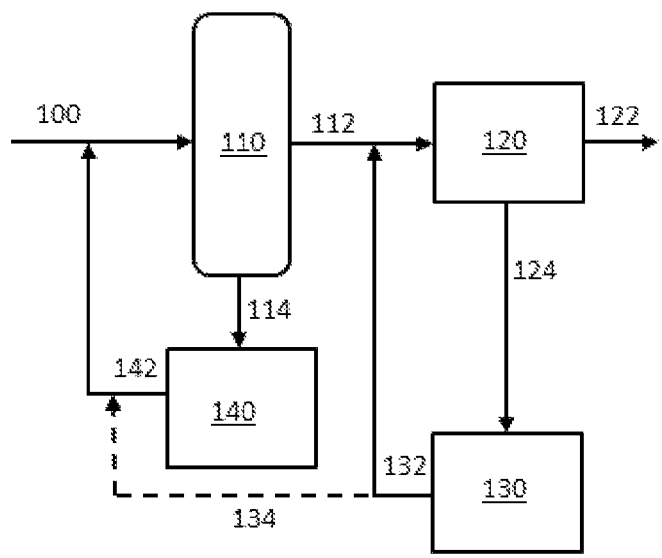
FIG. 1 is a schematic representation of one embodiment of the inventive process.

With reference to FIG. 1, in a first embodiment of the inventive process, a $C_8$ aromatic hydrocarbon mixture 100 comprising para-xylene, ortho-xylene and meta-xylene is provided to an ortho-xylene splitter 110, which may be a fractional distillation column, selective sorption unit, or any other technology known in the art. The $C_8$ aromatic hydrocarbon mixture 100 may be derived from any $C_{8+}$ aromatic hydrocarbon stream from which the ethylbenzene has been depleted or reduced by any means known in the art. The $C_8$ aromatic hydrocarbon mixture 100 may also be a $C_{8+}$ aromatic hydrocarbon stream produced by a process that produces low amounts of ethylbenzene, such as, but not limited to, a para-xylene selective aromatic alkylation product stream, a non-selective (equilibrium para-xylene) aromatic alkylation product stream, an aromatic disproportionation stream, an aromatic transalkylation stream, a methanol/dimethyl ether to aromatic product stream, a syngas to aromatic product stream, a $C_2$-$C_4$ alkane/alkene to aromatic product stream, an import stream, and/or an offspec para-xylene stream from a para-xylene recovery unit.

The ortho-xylene splitter 110 separates a first stream 112 comprising para-xylene and meta-xylene from a second stream 114 comprising ortho-xylene. The first stream 112 comprising para-xylene and meta-xylene is passed to a para-xylene recovery unit 120 to recover a para-xylene product 122 and leave a para-xylene-depleted stream 124 comprising meta-xylene. Preferably, the para-xylene-depleted stream 124 comprising meta-xylene consists essentially of meta-xylene. In one embodiment, the para-xylene product stream comprises at least 50 wt % para-xylene, preferably at least 60 wt % para-xylene, more preferably at least 70 wt % para-xylene, even preferably at least 80 wt % para-xylene, still even preferably at least 90 wt % para-xylene, and most preferably at least 95 wt % para-xylene, based on the total weight of the para-xylene product stream.

The para-xylene recovery unit 120 can include one or more of any of the para-xylene recovery units known in the art, including, for example, a crystallization unit, an adsorption unit (such as a PAREX™ unit or an ELUXYL™ unit), a reactive separation unit, a membrane separation unit, an extraction unit, a distillation unit, an extractive distillation unit, a fractionation unit, or any combination thereof. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and the previously-mentioned "Handbook of Petroleum Refining Processes".

The para-xylene-depleted stream 124 comprising meta-xylene is sent to a meta-xylene isomerization unit 130 where the meta-xylene stream 124 is contacted with a xylene isomerization catalyst under at least partially liquid phase conditions effective to isomerize the meta-xylene stream 124. Suitable conditions include a temperature of from about 400° F. (about 204° C.) to about 1,000° F. (about 538° C.), preferably from about 482° F. (250° C.) to about 572° F. (300° C.), more preferably about 482° F. (250° C.) to about 527° F. (275° C.); a pressure of from about 0 to 1,000 psig (6.9 MPa), preferably from about 350 psig (2.41 MPa) to about 500 psig (3.45 MPa), more preferably about 350 psig (2.41 MPa) to about 400 psig (2.75 MPa); and a weight hourly space velocity (WHSV) of from 0.5 to 100 $hr^{-1}$, preferably from 0.5 to 10 $hr^{-1}$, more preferably from 0.5 to 5 $hr^{-1}$, with the pressure and temperature being adjusted within the above ranges to ensure that at least part of the meta-xylene stream 124 is in the liquid phase. Generally, the conditions are selected so that at least 50 wt % of the meta-xylene stream 124 would be expected to be in the liquid phase.

The catalyst used in the meta-xylene isomerization unit 130 is a ZSM-23 zeolite with a MTT structure type that has a $SiO_2/Al_2O_3$ ratio between 15-75, preferably between 15-50, an external surface area of at least 75 $m^2/g$, preferably at least 90 $m^2/g$, most preferably about 105 to 115 $m^2/g$, and an average crystal size of 5 microns or less, or 2 microns or less, or 1 micron or less, or 0.1 microns or less, such as that disclosed in U.S. Pat. Nos. 5,332,566; 4,599,475; and 4,531,012, which are all incorporated herein by reference in their entireties.

External surface area may be calculated using the Brunauer-Emmett-Teller (BET) method. In the Brunauer-Emmett-Teller (BET) method, the overall surface area (also referred to as total surface area) of a molecular sieve may be measured using the adsorption-desorption of nitrogen by a solid at 77 K as the function of relative partial pressure. The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

Particle size is measured by averaging the size of multiple particles as shown in SEM images obtained on a HITACHI 54800 Field Emission Scanning Electron Microscope (SEM). The particle size is measured by averaging the size of multiple particles as shown in the SEM. The same method is used for crystal size. Transmission Electron Microscopy may also be used, but in event of conflict between SEM and TEM, SEM shall control.

In one embodiment, the ZSM-23 is self-bound.

In another embodiment, in addition to the zeolite, the catalyst employed in the meta-xylene isomerization unit 130 may include one or more binder or matrix materials resistant to the temperatures and other conditions employed in the process. Such materials include materials such as clays, silica, and/or metal oxides such as alumina. The latter may be either naturally occurring or in the form of gelatinous precipitates or gels including mixtures of silica and metal oxides. Said materials may suitably serve as diluents to control the amount of conversion in a given process so that products can be obtained economically and orderly without employing other means for controlling the rate of reaction. These materials may be incorporated to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst and diffusion of reactants and products from the active sites in the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the porous crystalline material can be composited with a porous matrix material such as silica, alumina, titania, zirconia, lanthanum oxide, yttrium oxide, zinc oxide, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. In addition other mixed metal oxides such as hydrotalcite, perovskite, spinels, and inverse spinels may be composited with the porous crystalline materials.

The relative proportions of porous crystalline material and optional inorganic oxide matrix vary widely, with the content of the porous crystalline material ranging from about 1 to about 90% by weight, and more usually in the range of about 2 to about 80 wt % of the composite. In an embodiment in which the catalyst composition includes an inorganic oxide matrix material, the matrix material preferably comprises about 35 wt % of alumina binder (making the balance of the catalyst comprise about 65 wt % ZSM-23).

The meta-xylene isomerization unit 130 isomerizes the meta-xylene in the para-xylene-depleted stream 124 and produces a first isomerized stream 132 containing para-xylene at higher than its equilibrium amount, that is at least about 24 wt % para-xylene, less than about 3 wt % ortho-xylene, with the balance being about 73 wt % meta-xylene, based on the amount of meta-xylene sent to the meta-xylene isomerization unit 130. Preferably, the meta-xylene isomerization unit 130 isomerizes the meta-xylene in the para-xylene-depleted stream 124 and produces at least about 27 wt % para-xylene, based on the total amount of xylenes. Any ortho-xylene remaining in the para-xylene-depleted stream 124 will pass through the meta-xylene isomerization unit 130 unconverted; thus, the amounts above are based on a pure meta-xylene stream. At least a portion of the first isomerized stream 132 then is recycled to the para-xylene recovery unit 120. At least a portion of the first isomerized stream 132 may also be sent to the ortho-xylene splitter 110 as purge stream 134 to prevent the build-up of ortho-xylene in the meta-xylene isomerization loop.

Because the meta-xylene isomerization unit 130 produces para-xylene in higher than equilibrium amounts, as compared to the equilibrium amounts obtained by prior art catalysts, and the isomerization units are capable of operating in the liquid phase, the inventive process decreases the recycle necessary to produce the same amount of para-xylene, resulting in increased efficiency and energy savings.

The second stream 114 comprising ortho-xylene may be sold as product or sent to an ortho-xylene isomerization unit 140 where the second stream 114 comprising ortho-xylene is contacted with a xylene isomerization catalyst under at least partially liquid phase conditions effective to isomerize the second stream 114 comprising ortho-xylene back towards an equilibrium concentration of the xylene isomers. Suitable conditions include a temperature of from about 400° F. (about 204° C.) to about 1,000° F. (about 538° C.), a pressure of from about 0 to 1,000 psig, a weight hourly space velocity (WHSV) of from 0.5 to 100 $hr^{-1}$, with the pressure and temperature being adjusted within the above ranges to ensure that at least part of the second stream 114 comprising ortho-xylene is in the liquid phase. Generally, the conditions are selected so that at least 50 wt % of the second stream 114 comprising ortho-xylene would be expected to be in the liquid phase.

Any catalyst capable of isomerizing xylenes in the liquid phase can be used in the ortho-xylene isomerization unit 140, but in one embodiment the catalyst comprises an intermediate pore size zeolite having a Constraint Index between 1 and 12. Constraint Index and its method of determination are described in U.S. Pat. No. 4,016,218, which is incorporated herein by reference. Particular examples of suitable intermediate pore size zeolites include ZSM-5, ZSM-11, ZSM-12, ZSM-22, ZSM-23, ZSM-35, ZSM-48, and MCM-22, with ZSM-5 and ZSM-11 being particularly preferred, specifically ZSM-5. It is preferred that the acidity of the zeolite, expressed as its alpha value, be greater than 300, such as greater than 500, or greater than 1000. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used to determine the alpha values cited herein include a constant temperature of 538° C. and a variable flow rate as described in detail in the Journal of Catalysis, Vol. 61, p. 395. The ortho-xylene isomerization unit 140 produces a second isomerized stream 142 containing xylenes at their equilibrium ratio, that is about 55 wt % meta-xylene, about 22 wt % ortho-xylene, and about 23 wt % para-xylene, based on the total amount of xylenes in the stream. The second isomerized stream 142 is recycled to the ortho-xylene splitter 110.

Figure 2:
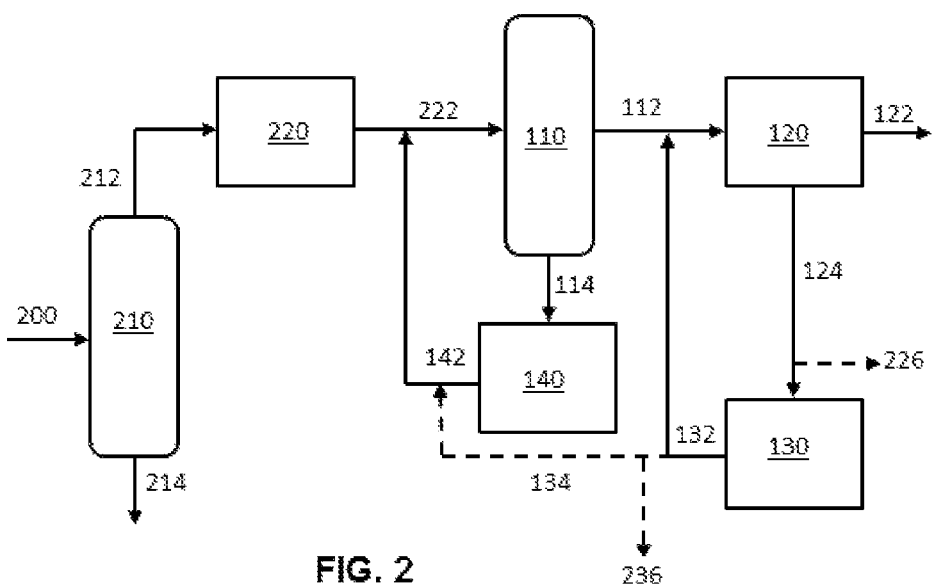
FIG. 2 is a schematic representation of another embodiment of the inventive process.

FIG. 2 shows an embodiment of the inventive process involving the removal of ethylbenzene. A $C_{8+}$ aromatic hydrocarbon stream 200 is separated into a $C_8$ aromatic hydrocarbon stream 212 and a $C_{9+}$ aromatic hydrocarbon stream 214 by a xylene splitter column 210. The $C_{8+}$ aromatic hydrocarbon stream 200 may be any hydrocarbon stream containing xylenes and ethylbenzene, such as, but not limited to, a reformate stream (product stream of a reformate splitting tower), a hydrocracking product stream, a xylene or ethylbenzene reaction product stream, an aromatic disproportionation stream, an aromatic transalkylation stream, a Cyclar™ process stream, and/or an import stream.

In one embodiment, the $C_8$ aromatic hydrocarbon stream 212 is passed to an ethylbenzene removal unit 220. The ethylbenzene removal unit 220 may be a fractionation column or an adsorption unit equipped with an ethylbenzene-selective adsorbent. The ethylbenzene-depleted mixed xylenes stream 222 is then passed to an ortho-xylene splitter 110 and follows the embodiment described with reference to FIG. 1. Because it is expected that ethylbenzene will be non-reactive with the ZSM-23, in another embodiment, where ethylbenzene removal unit 220 is not present, there is an ethylbenzene purge stream 226 taken prior to the meta-xylene isomerization unit 130 or an ethylbenzene purge stream 236 taken after the meta-xylene isomerization unit 130.

Figure 3:
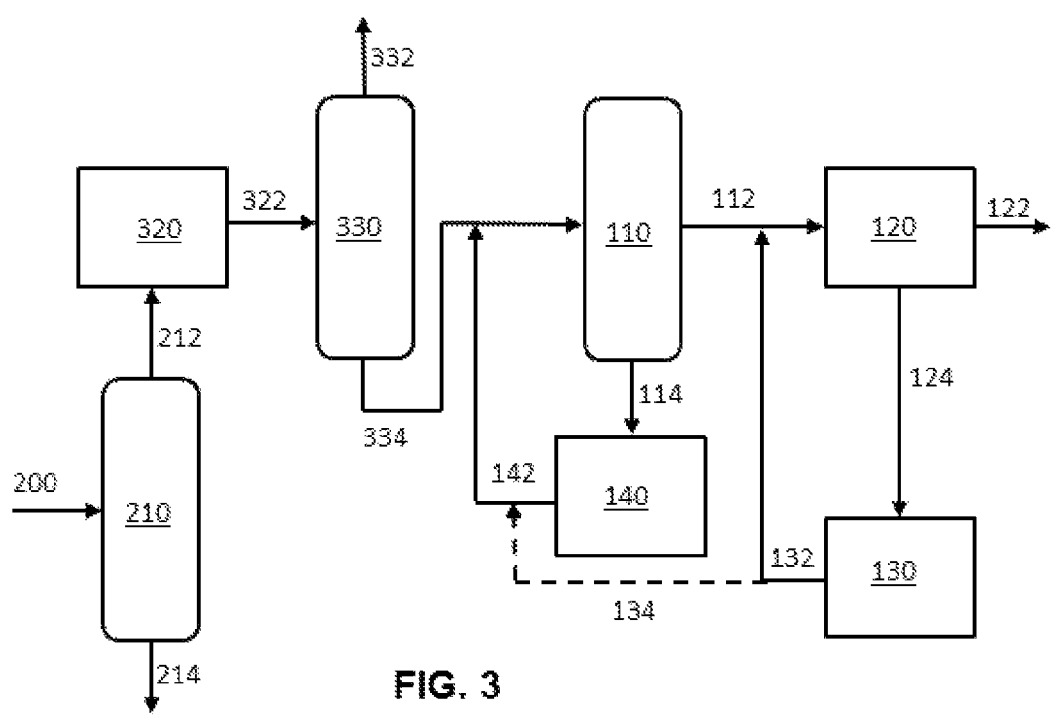
FIG. 3 is a schematic representation of a third embodiment of the inventive process.

FIG. 3 shows another embodiment of the inventive process involving the removal of ethylbenzene. As with the FIG. 2 embodiment, a $C_{8+}$ aromatic hydrocarbon stream 200 is separated into a $C_8$ aromatic hydrocarbon stream 212 and a $C_{9+}$ aromatic hydrocarbon stream 214 by a xylene splitter column 210. The $C_8$ aromatic hydrocarbon stream 212 is passed to an ethylbenzene conversion unit 320, where ethylbenzene is dealkylated to benzene. Although ethylbenzene removal can be carried out in liquid phase, it is preferably achieved in gas phase. Hydrogen is fed to the ethylbenzene conversion unit 320. Preferably, once-through low pressure hydrogen is used, thereby eliminating facilities for the recovery and recycle of hydrogen. In the ethylbenzene removal unit, the preferred catalyst is the first catalyst used in the dual bed catalyst system described in U.S. Pat. No. 5,516,956 or 7,663,010. However, other catalytic processes that accomplish dealkylating ethylbenzene to benzene known to those skilled in the art could be utilized, such as the first catalyst used in the dual bed catalyst system described in U.S. Pat. No. 7,271,118. The ethylbenzene removal process is preferably operated at conditions maximizing ethylbenzene conversion per pass, preferably >80 wt % conversion per pass, and even more preferably >90 wt % conversion per pass. Operating conditions for the ethylbenzene conversion unit 320 will also be chosen as to minimize undesirable transalkylation reactions leading to xylene losses to $C_7$, $C_9$, or $C_{10}$ aromatics.

The ethylbenzene-depleted stream 322 is then passed through a high pressure separator (not shown) to remove hydrogen-rich light gas before it is sent to a deheptanizer column 330. The overhead stream 332 of the deheptanizer column 330 mostly contains $C_6$ and $C_7$ aromatic hydrocarbons and may be sent to further processing. The bottoms stream 334 comprising mixed xylenes is passed to an ortho-xylene splitter 110 and follows the embodiment described with reference to FIG. 1.

The invention will now be more particularly described with reference to the following non-limiting Examples.

Example 1—Synthesis of ZSM-5

ZSM-5 was made as disclosed in U.S. Pat. Nos. 3,702,886; 3,790,471; 3,755,145; and 3,843,741, the disclosures of which are all incorporated in their entireties. The synthesized ZSM-5 had a MFI structure type with a $SiO_2/Al_2O_3$ ratio between 40 and 60 and an average crystal size of less than 0.05 microns. The elemental analysis of the synthesized ZSM-5 is shown below in Table 1, determined by method AM-I 1073 in which the amount of silica, alumina, sodium and potassium in a catalyst sample is found by inductively coupled plasma atomic emission spectroscopy (ICP-AES).

TABLE 1

Elemental analysis of ZSM-5

| Component | Wt % |
|---|---|
| Alumina ($Al_2O_3$) | 2.80 |
| Sodium (Na) | <0.005 |
| Silica ($SiO_2$) | 88.3 |
| Potassium (K) | <0.01 |
| Water ($H_2O$) | Balance |

Example 2—Synthesis of ZSM-23-A

ZSM-23-A was made as disclosed in U.S. Pat. Nos. 5,332,566; 4,599,475; and 4,531,012, the disclosures of which are all incorporated in their entireties. The resulting product has a XRD pattern equivalent to ZSM-23 with the majority of the crystal having a crystallite size below 0.1 microns as determined by transmission electron microscopy (TEM), and external surface area of 110 $m^2/g$, and a $SiO_2/Al_2O_3$ ratio of about 35. This crystal was then extruded with 65% zeolite and 35 wt % Versal alumina, exchanged with an ammonium salt and calcined to prepare the acid from of the zeolite. The calcined extrudate was then sized to 40-60 mesh for catalytic testing.

Example 3—Comparison of ZSM-5 and ZSM-23-A for Xylenes Isomerization

The ZSM-5 as synthesized in Example 1 and the ZSM-23-A as synthesized in Example 2 were tested in a meta-xylene isomerization process using similar conditions. The conditions used and results obtained are shown below in Table 2. The WHSV was chosen to maintain constant meta-xylene conversion in order to accurately compare selectivity to para-xylene.

TABLE 2

Comparison of ZSM-5 and ZSM-23-A in meta-xylene isomerization

| Catalyst | ZSM-5 (Example 1) | ZSM-23-A (Example 2) |
|---|---|---|
| Temperature (° C.) | 260 | 260 |
| Weight Hourly Space Velocity ($hr^{-1}$) | 34 | 5.1 |
| Feed composition | 99.8 wt % meta-xylene | 99.8 wt % meta-xylene |
| Pressure (bar-a/MPa) | 1.6/0.16 | 1.3/0.13 |
| Meta-xylene conversion (%) | 7 | 7 |
| Ratio of para-xylene/ortho-xylene formed | 4.0 | 11.8 |
| Selectivity to para-xylene (%) | 80 | 92 |

As Table 2 shows, the ZSM-23-A with a small crystal size is more selective to para-xylene than ortho-xylene, and thus produces a para-xylene in an amount higher than its equilibrium concentration.

Example 4—Synthesis of ZSM-23-B

ZSM-23-B was made as disclosed in U.S. Pat. Nos. 5,332,566; 4,599,475; and 4,531,012, the disclosures of which are all incorporated in their entireties. The resulting product has a XRD pattern equivalent to ZSM-23 with the majority of the crystal having a crystallite size of about 1-2 microns as determined by scanning electron microscopy (SEM), external surface area of about 60 $m^2/g$, and a $SiO_2/Al_2O_3$ ratio of about 73. The crystal was extruded with 0% binder.

Example 5—Synthesis of ZSM-23-C

ZSM-23-C was synthesized as described above in Example 2, but the resulting to crystals were not extruded with alumina binder. As in Example 2, the resulting product has a XRD pattern equivalent to ZSM-23 with the majority of the crystal having a crystallite size below 0.1 microns as determined by transmission electron microscopy (TEM), external surface area of about 110 $m^2/g$, and a $SiO_2/Al_2O_3$ ratio of about 35.

Example 6—Comparison of ZSM-23-B and ZSM-23-C for Xylenes Isomerization

The ZSM-23-B as made in Example 4 and the ZSM-23-C as made in Example 5 were tested in a meta-xylene isomerization process using similar conditions. The conditions used and results obtained are shown below in Table 3. The WHSV was chosen to maintain constant meta-xylene conversion in order to accurately compare selectivity to para-xylene.

TABLE 3

Comparison of ZSM-23-B and ZSM-23-C in meta-xylene isomerization

| Catalyst | ZSM-23-B (Example 4) | ZSM-23-C (Example 5) | ZSM-23-C (Example 5) |
|---|---|---|---|
| Temperature (° C.) | 260 | 260 | 260 |
| Weight Hourly Space Velocity ($hr^{-1}$) | 2.55 | 15.5 | 5.2 |
| Feed composition | 99.8 wt % meta-xylene | 99.8 wt % meta-xylene | 99.8 wt % meta-xylene |
| Pressure (bar-a/MPa) | 31/3.1 | 31/3.1 | 31/3.1 |
| Meta-xylene conversion (%) | 19 | 25 | 33 |
| Amount of meta-xylene in product (wt %) | 80.4 | 74.5 | 66.7 |
| Amount of para-xylene in product (wt %) | 17.6 | 23.3 | 28.7 |
| Amount of ortho-xylene in product (wt %) | 1.7 | 1.9 | 4.3 |
| Selectivity to para-xylene (%) | 91 | 92 | 86 |

As Table 3 shows, the smaller crystal size and higher $SiO_2/Al_2O_3$ ratio of the ZSM-23 affect the activity as more ZSM-23-B catalyst (lower WHSV) is necessary to achieve a certain conversion compared to ZSM-23-C catalyst. ZSM-23-C yields more para-xylene than ZSM-23-B at a given yield of ortho-xylene, further lending support that smaller crystal size and higher $SiO_2/Al_2O_3$ lead to improved performance. The para-xylene yield of 28.7 wt %, based on the total amount of xylenes, exceeds that of prior art catalysts, i.e., ZSM-5. Additionally, the smaller crystal size and lower $SiO_2/Al_2O_3$ ratio of ZSM-23-C (Example 5) provide the highest para-xylene yield at lower WHSV with only slightly lower para-xylene selectivity. Without wishing to be bound by theory, given that isomerization is likely to be occurring in the pore mouth of the ZSM-23, the smaller crystal gives more sites for the isomerization to occur, allowing for the reaction to be run at higher space velocities. In addition, the increased aluminum content in the zeolite provides more acid sites at the pore mouth, thereby creating more active sites in the zeolite. Coupling the small crystal size and increased aluminum content is one possible explanation for the increase in the conversion while minimizing any deleterious effects on the selectivity of the catalyst.

As seen by comparing Example 3 with Example 6, binding the ZSM-23 with alumina affects the conversion but not the selectivity. Example 3 uses ZSM-23-A which is bound with alumina while Example 6 uses the same ZSM-23 without a binding. The unbound catalyst shows significantly better meta-xylene conversion, while maintaining a high para-xylene selectivity.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing para-xylene comprising:
  contacting a feed stream comprising meta-xylene with a first catalyst comprising ZSM-23 having a $SiO_2/Al_2O_3$ ratio between 15 and 75 and an external surface area of at least 75 m²/g under at least partially liquid phase conditions effective to produce a first isomerized stream comprising para-xylene having a para-xylene content of more than 24 wt %, based on the total amount of xylenes in the first isomerized stream;
  wherein said feed stream comprising meta-xylene is produced by:
    (a) providing a $C_8$ aromatic hydrocarbon mixture comprising para-xylene, ortho-xylene and meta-xylene to an ortho-xylene splitter;
    (b) recovering a first stream comprising para-xylene and meta-xylene and a second stream comprising ortho-xylene; and
    (c) recovering para-xylene from the first stream comprising para-xylene and meta-xylene in a para-xylene recovery unit, and
  wherein the second stream comprising ortho-xylene is contacted with a second catalyst comprising ZSM-5 having an alpha value of at least 300 under at least partially liquid phase conditions effective to produce a second isomerized stream and the second isomerized stream is recycled back to the ortho-xylene splitter.

2. The process of claim 1, wherein the first catalyst comprises ZSM-23 having $SiO_2/Al_2O_3$ ratio between 15 and 50 and an external surface area of at least 90 m²/g.

3. The process of claim 1, wherein the first catalyst is self-bound.

4. The process of claim 1, wherein the feed stream consists essentially of meta-xylene.

5. The process of claim 1, wherein the contacting of the feed stream with the first catalyst is conducted under at least partially liquid phase conditions comprising a temperature from 400° F. (204° C.) to 1,000° F. (538° C.), a pressure of from 0 to 1,000 psig, a weight hourly space velocity (WHSV) of from 0.5 to 100 hr$^{-1}$.

6. The process of claim 5, wherein the contacting of the feed stream with the first catalyst is conducted under at least partially liquid phase conditions comprising a temperature from 482° F. (250° C.) to 572° F. (300° C.), a pressure from 350 psig (2.41 MPa) to 500 psig (3.45 MPa), and a weight hourly space velocity (WHSV) from 0.5 to 10 hr$^{-1}$.

7. The process of claim 1, wherein the para-xylene recovery unit comprises an adsorptive separation unit or a crystallization unit.

8. The process of claim 1, wherein at least a portion of the first isomerized stream is recycled back to the para-xylene recovery unit.

* * * * *